United States Patent
Klemm (10) Patent No.: US 11,730,404 B2
(45) Date of Patent: Aug. 22, 2023

(54) IMPLANTABLE GLUCOSE MONITOR

(71) Applicant: SANOFI, Paris (FR)

(72) Inventor: Thomas Klemm, Frankfurt am Main (DE)

(73) Assignee: Sanofi, Paris (FR)

( * ) Notice: Subject to any disclaimer, the term of this patent is extended or adjusted under 35 U.S.C. 154(b) by 421 days.

(21) Appl. No.: 16/765,231

(22) PCT Filed: Nov. 15, 2018

(86) PCT No.: PCT/EP2018/081303
§ 371 (c)(1),
(2) Date: May 19, 2020

(87) PCT Pub. No.: WO2019/101611
PCT Pub. Date: May 31, 2019

(65) Prior Publication Data
US 2020/0275866 A1     Sep. 3, 2020

(30) Foreign Application Priority Data
Nov. 21, 2017 (EP) ..................... 17306606

(51) Int. Cl.
*A61B 5/1455* (2006.01)
*A61B 5/145* (2006.01)
(Continued)

(52) U.S. Cl.
CPC .......... *A61B 5/14532* (2013.01); *A61B 5/076* (2013.01); *A61B 5/1459* (2013.01);
(Continued)

(58) Field of Classification Search
CPC ... A61B 5/1455; A61B 5/14532; A61B 5/076; A61B 5/14558; A61B 5/1459; A61B 5/6876
See application file for complete search history.

(56) References Cited

U.S. PATENT DOCUMENTS

| 4,704,029 A | 11/1987 | Van Heuvelen et al. |
| 6,122,536 A | 9/2000 | Sun et al. |

(Continued)

FOREIGN PATENT DOCUMENTS

| JP | H11-508792 | 8/1999 |
| JP | 2013-509944 | 3/2013 |

(Continued)

OTHER PUBLICATIONS

PCT International Preliminary Report on Patentability in Application No. PCT/EP2018/081303, dated May 26, 2020, 8 pages.

(Continued)

*Primary Examiner* — Marjan Fardanesh
(74) *Attorney, Agent, or Firm* — Fish & Richardson P.C.

(57) ABSTRACT

Implantable device for measuring the glucose concentration of a body fluid when implanted, the device comprising a glucose measurement unit, the glucose measurement unit comprising a light source configured to emit light towards a light transmissive part of a housing of the device, the device further comprising an optical sensor configured to detect light returned through the transmissive part from the light source, and output an electrical signal based on the detected light, and a wireless communication module configured to wirelessly communicate with an external wireless communication device, wherein the wireless communication module is configured to wirelessly transmit a signal based on the electrical signal to the external wireless communication device.

20 Claims, 5 Drawing Sheets

(51) Int. Cl.
　　　*A61B 5/07*　　　　(2006.01)
　　　*A61B 5/1459*　　 (2006.01)
　　　*A61B 5/00*　　　　(2006.01)
　　　*G01N 33/49*　　　(2006.01)

(52) U.S. Cl.
　　　CPC ........ *A61B 5/14558* (2013.01); *A61B 5/6861* (2013.01); *G01N 33/49* (2013.01); *A61B 2560/0219* (2013.01); *A61B 2560/0252* (2013.01)

(56) References Cited

U.S. PATENT DOCUMENTS

| | | |
|---|---|---|
| 2002/0016535 A1 | 2/2002 | Martin et al. |
| 2004/0011671 A1 | 1/2004 | Shults et al. |
| 2010/0160749 A1 | 6/2010 | Gross et al. |
| 2014/0350365 A1 | 11/2014 | Sato |

FOREIGN PATENT DOCUMENTS

| | | |
|---|---|---|
| JP | 2013-126509 | 6/2013 |
| JP | 2016-502420 | 1/2016 |
| WO | WO 1997/001986 | 1/1997 |
| WO | WO 2005/063117 | 7/2005 |
| WO | WO 2011/056274 | 5/2011 |
| WO | WO 2014/070456 | 5/2014 |
| WO | WO 2015/084269 | 6/2015 |

OTHER PUBLICATIONS

PCT International Search Report and Written Opinion in Application No. PCT/EP2018/081303, dated Dec. 3, 2018, 11 pages.

IMPLANTABLE GLUCOSE MONITOR

CROSS REFERENCE TO RELATED APPLICATIONS

The present application is the national stage entry of International Patent Application No. PCT/EP2018/081303, filed on Nov. 15, 2018, and claims priority to Application No. EP 17306606.9, filed on Nov. 21, 2017, the disclosures of which are incorporated herein by reference.

TECHNICAL FIELD

The present disclosure relates to an implantable device for measuring the glucose concentration of a body fluid when implanted, a system comprising an implantable device, and a method for measuring glucose concentration.

BACKGROUND

Insulin therapy often generally requires repeated blood glucose measurements to be taken from a diabetic patient. Diabetics with Type I diabetes may measure blood glucose 5-9 times a day, while those with gestational diabetes may take measurements up to 11 times per day.

Known blood glucose testing methods involve collecting a blood sample from a patient using a lancet. Blood collection using a lancet may be painful and unpleasant for a diabetic, particularly if a high testing frequency is required. Repeated blood collection from a skin site may lead to the formation of scars or calluses, or increased nerve density, which in turn can make it difficult to collect blood.

SUMMARY

According to an aspect of the present disclosure, there is provided an implantable device for measuring the glucose concentration of a body fluid when implanted, the implantable device comprising: a glucose measurement unit comprising a first light source configured to emit light towards a light transmissive part of a housing of the device and a first optical sensor configured to detect light returned through the light transmissive part from the first light source, and output a first electrical signal based on the detected light; and a wireless communication module configured to wirelessly communicate with an external wireless communication device, wherein the wireless communication module is configured to wirelessly transmit a signal based on the first electrical signal to the external wireless communication device. The implantable device allows for continuous remote monitoring of glucose levels within a patient into which the device is implanted, without the need for collecting blood samples using a lancet or similar device.

The wireless communication module may be configured to wirelessly receive power from the external wireless communication device. This is advantageous in that it provides an implantable device that does not require replacement of an internal power source such as a non-rechargeable battery. The implantable device may therefore be repeatedly used to monitor glucose levels over a long period of time without the need to replace the device due to a run-down battery. In some examples, the device may comprise a rechargeable power source such as a battery, wherein the power source is recharged by the power received by the wireless communication module.

The implantable device may be dimensioned to be implantable into a human blood vessel, or tissue well perfused by a body fluid such as blood. This is advantageous since it allows for an accurate measurement of the patient's blood glucose.

An outer surface of the housing may comprise a recess, wherein the recess comprises at least part of the light transmissive part. This is advantageous in that may facilitate movement of body fluid such as blood or interstitial fluid around the implantable device, ensuring that the body fluid around the device is not stagnant, and hence providing a more accurate glucose reading. In some examples, the outer surface of the housing may comprise one or more projections, again to facilitate movement of body fluid around the implantable device. In some examples, the recess may be formed from one or more protrusions of the housing. Although the presence of a recess may be described in combination with other features in various embodiments herein, the presence of the recess is not mandatory, The implantable device may further comprise at least one lens arranged to focus the light emitted from the first light source towards a point outside the housing. This allows for accurate measurement of glucose concentration within the body fluid surrounding the housing, while reducing interference from external light sources such as ambient light.

The light emitted from the first light source may be linearly polarised and emitted through the light transmissive part to a first region outside the housing. The first optical sensor may be configured to detect linearly polarised light returned through the transmissive part from the first region outside the housing that has been optically rotated. The first optical sensor may be further configured to output the first electrical signal based on the detected optically rotated light. This provides a simple arrangement for determining the glucose concentration in a body fluid.

According to some embodiments, the implantable device may further comprise a first linear polarizer arranged to linearly polarize the light emitted from the first light source in a first plane, a second linear polarizer arranged to linearly polarize light from the first region outside the housing in a second plane substantially orthogonal to the first plane, and a third linear polarizer arranged to linearly polarize light from the first region outside the housing in a third plane, wherein the third plane is parallel to the first plane. The glucose measurement unit may further comprise a second optical sensor configured to detect light returned through the light transmissive part, and output a second electrical signal based on the detected light. The second linear polarizer may be arranged such that a first part of the linearly polarized light emitted from the first light source to the first region outside the housing is incident on the second linear polarizer. The third linear polarizer may be arranged such that a second part of the linearly polarized light emitted from the first light source to the first region outside the housing is incident on the third linear polarizer. The first optical sensor may be arranged to detect the first part of the linearly polarized light passing from the first region outside the housing through the second linear polarizer, and the second optical sensor may be arranged to detect the second part of the linearly polarized light passing from the first region outside the housing through the third linear polarizer. This arrangement provides a simple means for determining the glucose concentration in a body fluid, with improved interference suppression.

According to some embodiments, the glucose measurement unit may further comprises a second light source configured to emit light through the light transmissive part to a second region outside the housing, and a second optical sensor configured to detect light returned through the transmissive part, and output a second electrical signal based on the detected light. The implantable device may further comprise a first linear polarizer arranged to linearly polarize light emitted from the first light source in a first plane, a second linear polarizer arranged to linearly polarize light from the first region outside the housing in a second plane substantially orthogonal to the first plane, a third linear polarizer arranged to linearly polarize light emitted from the second light source in a third plane, and a fourth linear polarizer arranged to linearly polarize light from the second region outside the housing in a fourth plane, wherein the fourth plane is parallel to the third plane. The second linear polarizer may be arranged such that at least part of the linearly polarized light emitted from the first light source to the first region outside the housing is incident on the second linear polarizer. The fourth linear polarizer may be arranged such that at least part of the linearly polarized light emitted from the second light source to the second region outside the housing is incident on the fourth linear polarizer. The first optical sensor may be configured to be able to detect the at least part of the linearly polarized light emitted from the first light source, via the second linear polarizer. The second optical sensor may be configured to be able to detect the at least part of the linearly polarized light emitted from the second light source, via the fourth linear polarizer. This arrangement provides a simple arrangement for determining the glucose concentration in a body fluid, with improved interference suppression.

According to some embodiments, the glucose measurement unit is a refractometer. This arrangement provides a simple means for determining the glucose concentration in a body fluid.

The refractometer may comprise a prism, wherein the first light source and the prism are arranged such that the light emitted from the first light source is incident on a surface of the prism, via the prism, and wherein the first optical sensor is arranged to detect a portion of the light emitted from the first light source that is reflected at the surface of the prism, via the prism. This arrangement provides a particularly simple arrangement for determining the glucose concentration in a body fluid.

According to some embodiments, the glucose measurement unit is an infra-red spectrometer, the light emitted by the first light source is infra-red light and is emitted through the light transmission part to a region outside the housing, and the first optical sensor is configured to detect infra-red light returned through the light transmissive part from the first light source, via the region outside the housing, and output a first electrical signal based on the detected light infra-red light. This arrangement provides a simple means for determining the glucose concentration in a body fluid, with improved interference suppression.

According to some embodiments, the implantable device further comprises a temperature sensor, wherein the wireless communication module is configured to wirelessly transmit a signal based on a temperature measured by the temperature sensor to the external wireless communication device. This arrangement allows for temperature effects to be easily taken into account when processing the output of the glucose monitoring unit to determine a glucose concentration, thus providing a more accurate value of glucose concentration.

According to some embodiments, there is provided an implantable device for measuring the glucose concentration of a body fluid, the device comprising a housing containing: a glucose measurement unit comprising: a light source configured to emit light at least to an interface between the implantable device and the body fluid, when the implantable device is surrounded by body fluid; and an optical sensor configured to detect at least part of the light emitted from the light source via the interface, when the implantable device is surrounded by body fluid, and output an electrical signal based on the detected light; and a wireless communication module configured to wirelessly communicate with an external wireless communication device; wherein the wireless communication module is configured to wirelessly transmit a signal based on the electrical signal to the external wireless communication device.

According to another aspect of the present disclosure, there is provided a system comprising an aforementioned implantable device and an external wireless communication device, wherein the wireless communication module of the implantable device is configured to wirelessly transmit the signal based on the first electrical signal to the external wireless communication device. The system allows for simple and unobtrusive measurements of glucose concentration in a body fluid.

The external wireless communication device may be a smartphone. This is a particularly simple means for wirelessly communicating with the implantable device.

According to another aspect of the present disclosure, there is provided a method comprising emitting light, by a first light source of an implantable device for measuring the glucose concentration of a body fluid when implanted, towards a light transmissive part of a housing of the implantable device; detecting, by a first optical sensor of the implantable device, light returned through the transmissive part from the first light source; outputting, by the first optical sensor, a first electrical signal based on the detected light; and wirelessly transmitting, by a wireless communication module of the implantable device, a signal based on the first electrical signal to an external wireless communication device. This method allows for simple and unobtrusive measurements of glucose concentration in a body fluid.

These as well as other advantages of various aspects of the present disclosure will become apparent from the embodiments described hereinafter.

BRIEF DESCRIPTION OF THE FIGURES

Exemplary embodiments of the present disclosure are described with reference to the accompanying drawings, in which.

Reference will now be made in detail to the embodiments of the present disclosure, examples of which are illustrated in the accompanying drawings, wherein like reference numerals refer to like elements throughout.

DETAILED DESCRIPTION

An implantable device for measuring the glucose concentration of a body fluid when implanted is provided. A system comprising the implantable device and an external wireless communication device, and a method of measuring the glucose concentration of a body fluid using the implantable device and external wireless communication device are also provided.

The aforementioned body fluid is a fluid within a human or animal that contains glucose, wherein the glucose concentration can be measured for insulin therapy. The body fluid is preferably blood, but may alternatively or additionally be interstitial fluid. It is preferable to measure the glucose concentration in the blood of a human or animal rather than the interstitial fluid because blood is generally more responsive to changes in glucose concentration than interstitial fluid.

Figure 1A:
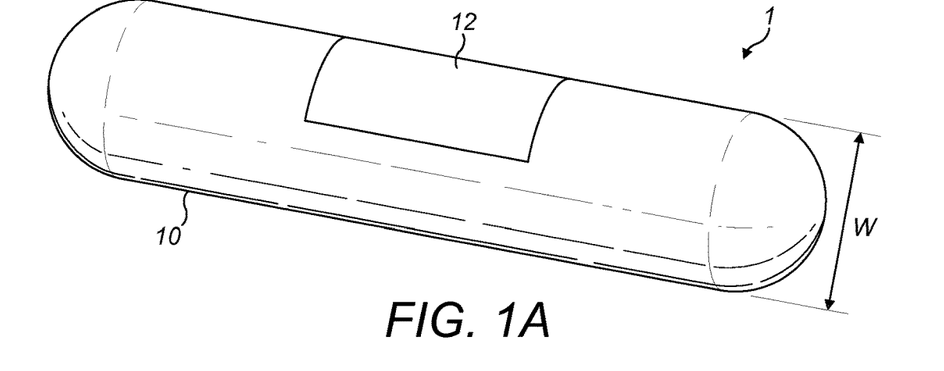
FIG. 1A is a front view of an implantable device according to embodiments of the present disclosure.

FIG. 1 shows an implantable device 1 in accordance with some aspects of the present disclosure. The implantable device 1 has a housing 10, wherein other components of the implantable device 1 are located inside the housing 10.

The housing 10 has a light transmissive part 12 which allows light of one or more wavelengths to pass through from one side of the light transmissive part 12 to another side. Light is therefore able to pass from outside the housing 10 to the inside of the housing 10 via the light transmissive part 12, and vice versa. A discrete region or window of the housing 10 may comprise the light transmissive part 12, as shown in FIG. 1A. Alternatively, the entire housing 10 may be light transmissive. In some examples, the light transmissive part 12 comprises a plurality of discrete regions of the housing 10, the discrete regions being separated by optically opaque parts of the housing 10.

The housing 10 is preferably made of a biocompatible material such as glass so that the implantable device 1 may be safely implanted into a human or animal. The use of glass for the housing 10 is advantageous in that glass is light transmissive, and hence the housing 10 and light transmissive part 12 may be formed from the same material, in a single process.

The implantable device 1 is to be subcutaneously implanted within a human or animal body. Preferably the implantable device 1 can be implanted within a blood vessel of the human or animal, allowing for measurement of the glucose concentration in the blood of said human or animal. In this case, the particular body fluid being measured will be blood.

In some embodiments the implantable device 1 is dimensioned to be implantable into a human blood vessel, such as an artery or vein. For example, the device may have a maximum width w along one axis of around less than 5 mm, preferably around less than 3 mm, and more preferably around 1.35 mm to 2 mm.

In some examples, the implantable device 1 configured is to be implanted into tissue well perfused by a body fluid, such as blood. For example, the implantable device 1 may be implanted within the interstitial fluid of a human or animal, for example just under the skin. In this case, the particular body fluid being measured is the interstitial fluid.

Once the implantable device 1 has been implanted, body fluid will come into contact with the light transmissive part 12 of the housing 10. When the implantable device 1 has been implanted in a blood vessel, blood will contact the light transmissive part 12. When the implantable device 1 has been implanted in interstitial fluid, interstitial fluid will be contacting the light transmissive part 12.

Figure 1B:
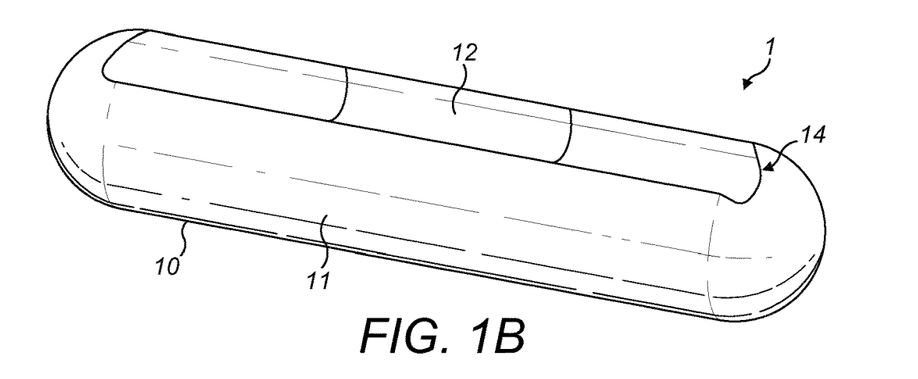
FIG. 1B is a front view of an implantable device having a recess according to embodiments of the present disclosure.
Figure 1C:
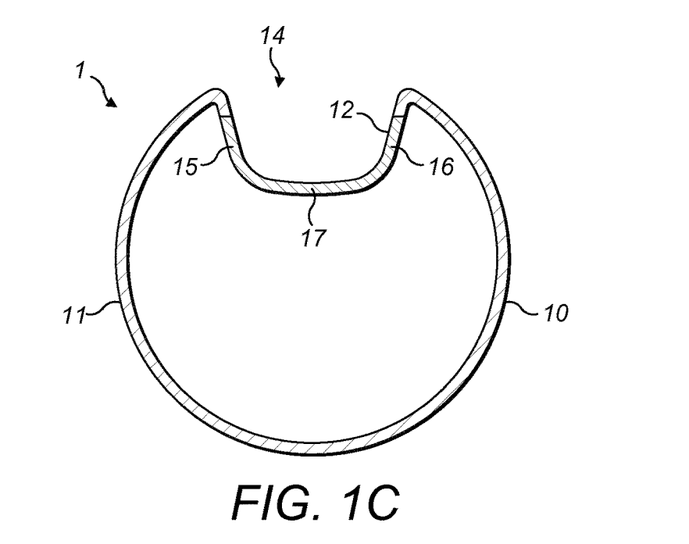
FIG. 1C is a schematic side-view cross-section of the implantable device of FIG. 1B.

FIG. 1B shows an implantable device 1 similar to the implantable device 1 of FIG. 1A, however an outer surface 11 of the housing 10 comprises a recess 14. FIG. 1C shows a side-view of the implantable device of FIG. 1B, showing a side-view of the recess 14.

As shown in FIG. 1C, the recess 14 may comprise a first side wall 15, a second side wall 16, and a bottom surface 17.

The recess 14 may be a groove in the outer surface 11 of the housing 10. In other embodiments, the recess 14 may be a conduit through which body fluid may flow from one side of the implantable device 1 to another side of the implantable device 1. For example, the conduit may extend from one side of the housing 10 to an opposing side of the housing 10. The recess 14 is filled with body fluid when the implantable device 1 is implanted.

Providing a recess 14 in the housing 10 can facilitate the movement of body fluid around the implantable device 1 when the device is implanted. This may be particularly advantageous if the implantable device 1 is implanted into a blood vessel, since the recess may allow blood to flow more easily around or through the implantable device 1. As such, blood flow through the blood vessel is less obstructed by the implanted device 1.

In some examples, the housing 10 may comprise one or more protrusions (not shown) arranged on the outer surface 11. The one or more protrusions may be configured to hold the implantable device 1 in a fixed location within a human or animal body once implanted into said body. If the implantable device 1 is implanted into a blood vessel, the one or more protrusions may be configured to hold the implantable device 1 in a fixed location within the blood vessel by exerting pressure on the inner walls of the blood vessel.

The light transmissive part 12 shown in FIGS. 1B and 1C is comprised in a discrete region of the housing 10, in this case entirely within recess 14. However, the light transmissive part 12 is not limited to this arrangement and may be located in another part of the housing 10, or may comprise the entirety of housing 10.

Figure 2:
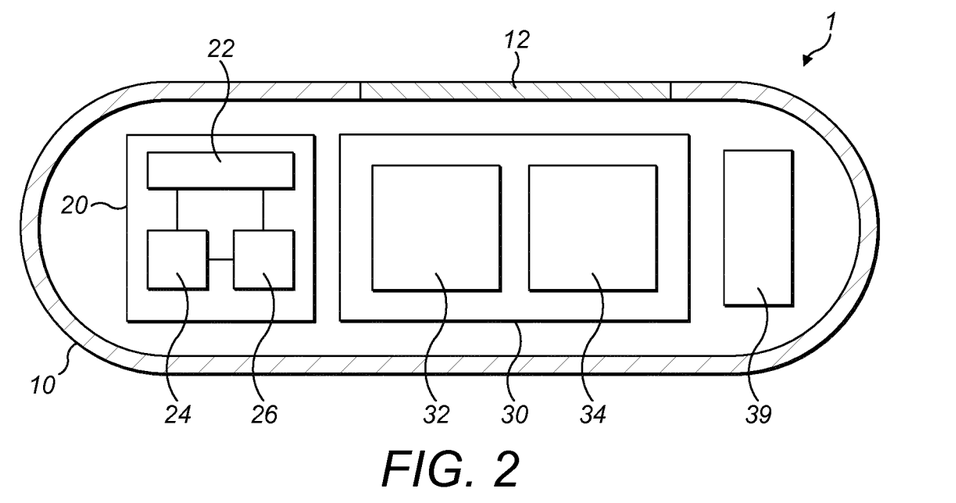
FIG. 2 is a schematic cross-section of an implantable device according to embodiments of the present disclosure.

FIG. 2 is a schematic cross-section of an implantable device 1 according to embodiments of the present disclosure.

The implantable device 1 comprises a wireless communication module 20, a glucose measurement unit 30, and a housing 10 having light transmissive part 12.

Figure 8:
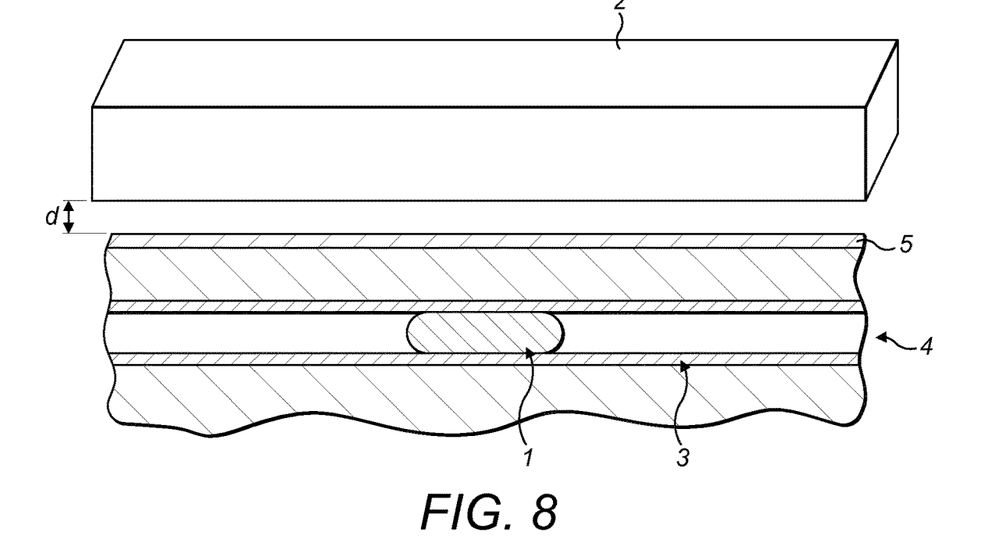
FIG. 8 is a schematic cross-section of a system comprising an implantable device and an external wireless communication device according to embodiments of the present disclosure, wherein the implantable device has been implanted into a blood vessel.

The wireless communication module 20 is configured to wirelessly communicate with an external wireless communication device 2 (as shown in FIG. 8), preferably using near field communication (NFC), but other forms of wireless communication may be used.

The wireless communication module 20 is preferably configured to wirelessly receive power from the external wireless communication 2 device by electromagnetic induction.

The wireless communication module 20 comprises an antenna 22, an energy storage unit 24 such as a capacitor or rechargeable battery, and a control unit 26 such as an integrated circuit. The antenna 22 is configured to transmit and receive wireless signals, wherein transmission of wireless signals by the antenna is controlled by the control unit 26. The energy storage unit 24 stores electrical energy received from the external wireless communication device 2 via the antenna 22. The control unit 26 may comprise a memory unit (not shown) for storing instructions to be carried out by the control unit 26, and/or data related to measurements made by the glucose measurement unit 30. The control unit 26 may control one or more operations of the glucose measurement unit 30 described herein, and may carry out any of the method steps described herein with respect to the implantable device 1.

The glucose measurement unit 30 comprises a light source 32 and an optical sensor 34. The light source 32 may comprise one or more light emitting diodes (LEDs), and is configured to emit light towards the light transmissive part 12 of the housing 10, that is, from the inside of the housing 10 towards the outside of the housing 10. The light source 32 is preferably powered by the energy storage unit 24 and controlled by the control unit 26.

The optical sensor 34, also known as a light sensor, detects light by converting received light into an electrical signal. The optical sensor 34 thus outputs an electrical signal based on the detected light. The optical sensor 34 may comprise one or more photodetectors such as photodiodes. The optical sensor 34 may detect light having a specific wavelength, or a range of wavelengths. The optical sensor 34 may be variable. That is, the specific wavelength or range of wavelengths detected by the optical sensor 34 may be variable. The wavelength(s) detected by such an optical sensor 34 may be selected by changing a voltage applied to the optical sensor 34.

The optical sensor 34 is configured to detect light returned through the light transmissive part 12 of the housing 10, and output an electrical signal based on the detected light. In other words, the optical sensor 34 is configured to detect light that has been emitted by the light source 32 from inside the housing 10 into the light transmissive part 12 of the housing 10 and that has returned to the inside of the housing 10 via the light transmissive part 12.

The returned light may have travelled from the light source 32 through the light transmissive part 12 to a region outside the housing 10, before returning back through the light transmissive part 12 to the inside of the housing 10 where it is detected by the optical sensor 34. In other examples the returned light has travelled from the light source 32 through the light transmissive part 12, before being internally reflected at a surface of the light transmissive part 12 and returning back through the light transmissive part 12 to the inside of the housing 10, where it is detected by the optical sensor 34. The surface of the light transmissive part 12 at which the light is internally reflected forms part of the outer surface 11 of the housing 10, and is in contact with body fluid when the implantable device 1 is implanted.

The wireless communication module 20 is configured to wirelessly transmit a signal based on the electrical signal output by the optical sensor to the external wireless communication device 2. In other words, the wireless communication module 20 is configured to wirelessly transmit a signal that is a function of the light detected by the optical sensor 34, whether this be a function of the intensity of the light, optical rotation of the light, or amount of refraction of the light. As such, the signal is also a function of the concentration of glucose in the body fluid in the vicinity of the implantable device 1.

The wireless signal transmitted by the wireless communication module 20 to the external wireless communication device 2 can be processed by the external wireless communication device 2, or a different apparatus, to provide an output which is dependent upon the glucose concentration of the body fluid being measured by the implantable device 1, such as a value of glucose concentration. The implantable device 1 may be calibrated by first performing a standard blood glucose test using a lancet.

In some embodiments, the implantable device 1 further comprises a temperature sensor 39, as shown in FIG. 2. The temperature sensor 39 is preferably located adjacent to or in the vicinity of the glucose measurement unit 30, but may be located anywhere within the implantable device 1 where it is desired to measure a temperature. The wireless communication module 20 may be configured to wirelessly transmit a signal based on a temperature measured by the temperature sensor 39 to the external wireless communication device 2. This signal may be a part of the aforementioned signal based on the electrical signal output by the optical sensor 34, or may be a separate signal.

Some of the measurements and operations performed by the glucose measurement unit 30 as described herein are temperature dependent. By providing a temperature sensor 39 and taking a temperature measurement, the temperature can be taken into account when processing or interpreting measurements made by the implantable device 1. The temperature sensor 39 is, however, optional, since a temperature could be measured using a device not forming part of the implantable device 1, or else could be approximated (for example it could be assumed that the temperature inside a human body is 37° C.).

Some optical properties of fluids such as body fluids vary with the concentration of glucose within the fluid. These optical properties include the specific rotation of the fluid (the angle of rotation of linearly polarized light passing through the fluid over a certain distance), the refractive index of the fluid, and the infrared absorption spectrum of the fluid. According to some aspects of the present disclosure, one or more of these properties can be directly or indirectly determined by the implantable device 1. By providing an output based upon one or more of these properties, a value for the concentration of glucose in a body fluid can be determined. The output is provided using the light source 32 configured to emit light towards the light transmissive part 12 of housing 10 of the implantable device 1, and the optical sensor 34 configured to detect light returned through the transmissive part 12 from the light source 32, wherein the output is an electrical signal based on the detected light, in particular the intensity of the detected light or the amount of refraction of the detected light.

As discussed previously, when the implantable device 1 is implanted, body fluid will contact light transmissive part 12, on an outer surface 11 of the housing 10. Light from the light source 32 passes through light transmissive part 12 and interacts with body fluid in contact with the light transmissive part 12. The interaction may occur outside the housing 10, within the body fluid itself, or at an interface between the body fluid and light transmissive part 12.

At least part of the light that has interacted with the body fluid returns through the light transmissive part 12 towards the inside of the housing 10 and is detected by optical sensor 34. Interaction between the body fluid and the light may involve optical rotation of the light by the body fluid, absorption of at least part of the light by the body fluid, or reflection and/or refraction of the light at the interface. Thus the light emitted by the light source 32 is in some manner modified by the glucose in the body fluid. The amount of interaction/modification is dependent upon the glucose concentration within the body fluid. The optical sensor 34 outputs an electrical signal based on the detected light, wherein the electrical signal will be a function of the amount of modification of the light by the body fluid, and hence a function of the glucose concentration in the body fluid.

The electrical signal may be processed within the implantable device 1, for example by control unit 26. The wireless communication module 20 receives the electrical signal from the optical sensor 34 and wirelessly transmits a signal based on the electrical signal to the external wireless communication device 2. In other words, the wirelessly transmitted signal is a function of the electrical signal, which is a function of the glucose concentration in the body fluid.

The signal transmitted by the wireless communication module 20 to the external wireless communication device 2 may be further processed by a processor (not shown) of the external wireless communication device 2 to provide a glucose concentration value for the body fluid.

According to some embodiments of the present disclosure, optical rotation of linearly polarised light passing through the body fluid is detected by the optical sensor 34.

Glucose is an optically active material. That is, the plane of polarization of linearly polarized light is rotated as it travels through glucose. For a solution of glucose, the rotation angle α of the plane of polarization of the linearly polarized light is dependent upon the concentration β of glucose in the solution, the path length L of the light through the solution, the wavelength λ of the light, and the temperature T of the glucose solution.

Specific rotation $[\alpha]T_\lambda$ is an intrinsic property of a compound in a solution and is the angle of rotation of the plane of polarization of a ray of monochromatic light that passes through a sample of a compound in a solution, per unit distance-concentration product.

Specific rotation is dependent upon temperature of the solution and wavelength of the polarized light. The concentration of glucose in a solution can be determined by measuring the angle α through which the plane of polarization of linearly polarized light is rotated as it travels through the solution, and the path length L of the linearly polarized light through the solution. If the temperature T of the solution and the wavelength λ of the linearly polarised light are known or approximated, then a value for the specific rotation $[\alpha]T_\lambda$ of glucose can be looked-up for that temperature and wavelength. The concentration β of glucose in the solution can then be determined from the angle α, specific rotation $[\alpha]T_\lambda$, and path length L according to the following equation:

$$[\alpha]_\lambda^T = \frac{\alpha}{\beta \cdot L}$$

It can be approximated that a significant amount of the optical rotation of linearly polarised light through a body fluid such as blood or interstitial fluid is caused by glucose rather than other components of the body fluid. The optical activity of other components in the body fluid can therefore generally be disregarded. Therefore by determining the angle of rotation of linearly polarized light passing through body fluid, a good approximation of the glucose concentration within the body fluid can be determined. Determination of the glucose concentration within the body fluid can be carried out by the implantable device 1, for example by the control unit 26, or by the external wireless communication device 2.

Determining the glucose concentration may comprise processing the electrical signal output by the optical sensor 34 or the signal based on the electrical signal that is wirelessly transmitted to the external wireless communication device 2, to determine a measurement value. A glucose concentration value may be determined by comparing the measurement value to a look-up table comprising a plurality of measurement values and their corresponding glucose concentration values.

Figure 3:
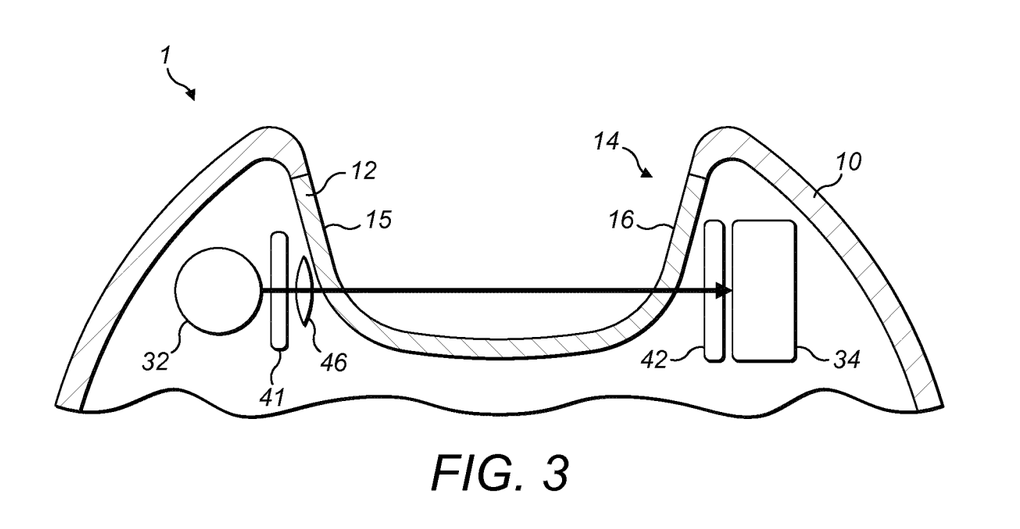
FIG. 3 is a schematic cross-section of part of an implantable device according to embodiments of the present disclosure.

FIG. 3 shows a partial schematic cross-section of an implantable device 1, such as the implantable device shown in FIG. 1B, wherein the glucose measurement unit 30 is configured to measure the rotation angle α of linearly polarized light travelling through the body fluid.

Figure 4:
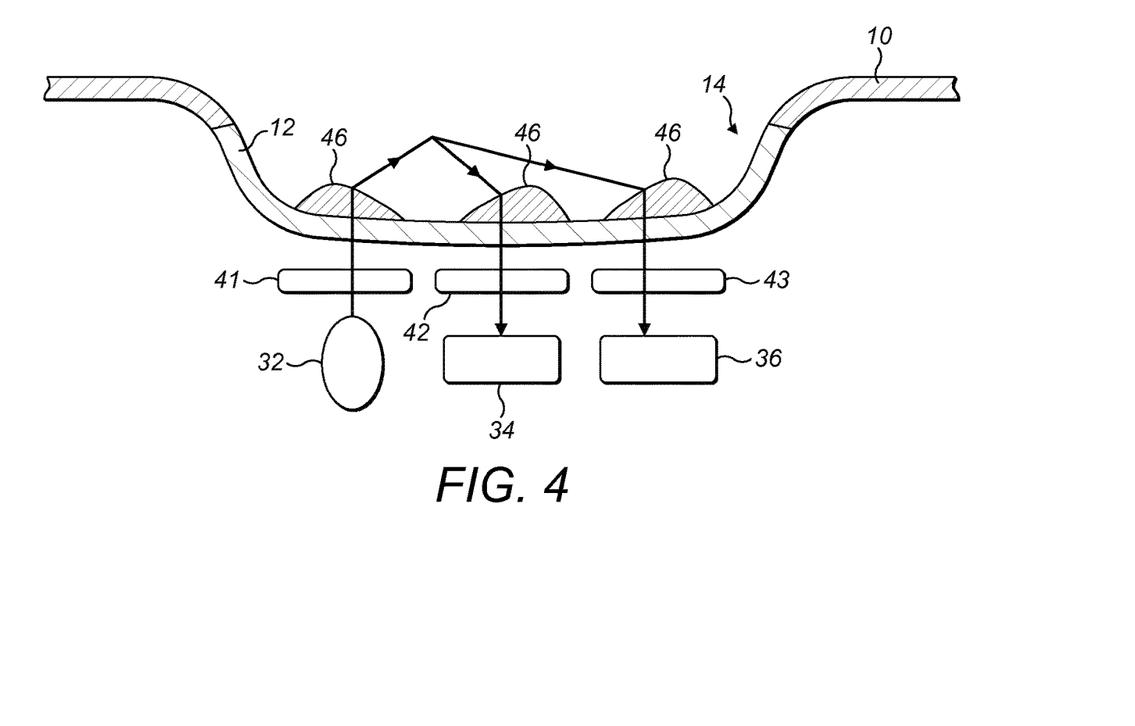
FIG. 4 is a schematic cross-section of part of an implantable device according to embodiments of the present disclosure.
Figure 5:
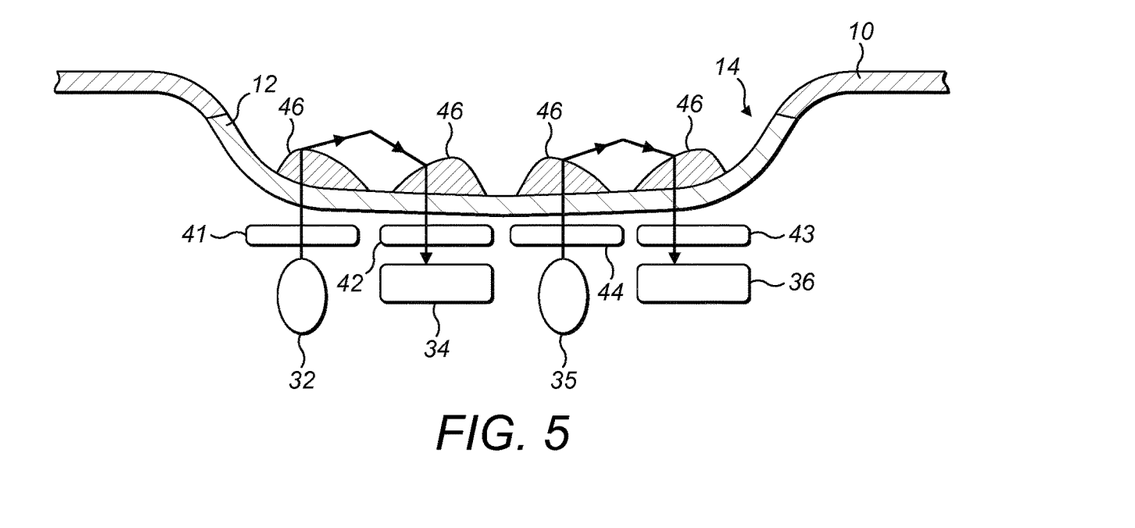
FIG. 5 is a schematic cross-section of part of an implantable device according to embodiments of the present disclosure.

The implantable device 1 of FIG. 3 is shown to comprise recess 14, however in some examples recess 14 may not be present. As shown in FIG. 3, the first side wall 15 and second side wall 16 of the recess 14 each comprise at least part of the light transmissive part 12. The light source 32 may be arranged within the housing 10 such that the light emitted towards the light transmissive part 12 passes through the light transmissive first side wall 15 to a region outside the housing, before returning through the light transmissive second side wall 16 to be detected by optical sensor 34, as indicated by the arrow in FIG. 3. In some examples the light source 32 and optical sensor 34 may be arranged within the housing 10 such that the emitted light leaves and returns through the same surface of the light transmissive part 12, for example bottom surface 17, as illustrated in FIG. 4 and FIG. 5.

As shown in FIG. 3, light emitted from light source 32 is linearly polarized by first linear polarizer 41 and emitted via light transmissive part 12 to a region outside the housing 10. This region will be within body fluid when the implantable device is implanted.

As with any of the embodiments disclosed herein, the implantable device 1 may comprise at least one lens 46 arranged to focus light emitted from the light source 32. In particular, the lens 46 may focus the light emitted from the first light source 32 towards a point outside the housing 10, or to focus light towards the optical sensor 34.

FIG. 3 shows the lens 46 located within the housing 10, in an optical path between light source 32 and light transmissive part 12, however lens 46 may instead be located in any suitable location such as on a surface of the light transmissive part 12, on outer surface 11 of the housing 10. FIG. 3 also shows first linear polarizer 41 located in an optical path between light source 32 and lens 46, however first linear polarizer 41 may in some examples be located along the optical path after the lens 46.

Linearly polarized light passing through the body fluid is optically rotated by the glucose within the body fluid so that the plane of polarization of the light is rotated by an amount dependent upon the concentration of the glucose and the distance travelled by the light through the glucose. The distance travelled by the light through the glucose can be determined prior to implantation of the device. The optical sensor 34 is configured to detect the optical rotation of the linearly polarised light that has passed through the body fluid and returned through the transmissive part 12 from the region outside the housing 10. The optical sensor 34 is further configured to output an electrical signal based on the detected optically rotated light. The output is based on the rotation angle α of the linearly polarized light.

As shown in FIG. 3, detecting the linearly polarised light returned through the transmissive part from the region outside the housing that has been optically rotated may comprise using a second linear polarizer 42 located in an optical path between the light source 32 and optical sensor 34, between the optical sensor 34 and the region outside the housing 10. The plane of polarization of the second linear polarizer 42 is rotated about the optical path with respect to the plane of polarization of the first linear polarizer 41, preferably such that it is substantially orthogonal to the plane of polarization of the first linear polarizer 41. As such, the amount of linearly polarized light from the light source 32 and first linear polarizer 41 detected by optical sensor 34 will be dependent upon the amount of optical rotation of the light. This optical rotation takes place as the linearly polarized light passes through the body fluid containing glucose. The amount of optical rotation, and therefore the amount of light detected by optical sensor 34 will depend upon the concentration of glucose in the body fluid. As such, the electrical signal output by the optical sensor 34 is based on the amount of optical rotation of the linearly polarized light and hence the concentration of glucose in the body fluid.

The implantable device 1 illustrated in FIG. 3 may be susceptible to interference, for example from the optical sensor 34 detecting light that does not originate from the light source 32, such as ambient light. FIG. 4 shows a partial schematic cross-section of an implantable device 1 similar to FIG. 3, but configured for greater interference suppression. As for the implantable device 1 shown in FIG. 3, the implantable device 1 shown in FIG. 4 comprises recess 14, but the presence of recess 14 is optional.

Similar to FIG. 3, the implantable device 1 shown in FIG. 4 comprises a light source 32, first linear polarizer 41 and second linear polarizer 42. However, here the glucose measurement unit 30 further comprises a second optical sensor 36. The first optical sensor 35 and second optical sensor 36 may each comprise one or more photodiodes.

As for the implantable device 1 of FIG. 3, the first linear polarizer 41 of FIG. 4 is arranged to linearly polarize light emitted from the light source 32 through the light transmissive part 12 in a first polarization plane, this polarized light being emitted to a region outside the housing 10. The second linear polarizer 42 is arranged to linearly polarize light from the region outside the housing 10 in a second polarization plane substantially orthogonal to the first plane (i.e. rotated 90° about the optical axis). A third linear polarizer 43 is arranged to linearly polarize light from the region outside the housing 10 in a third polarization plane, wherein the third plane is parallel to the first plane (i.e. rotated 0° about the optical axis).

FIG. 4 shows three lenses 46 configured to focus light as mentioned previously. One or more of the lenses 46 may be arranged to the focus light emitted from the light source 32 to a point or region outside the housing 10, in the body fluid. The first optical sensor 35 and second optical sensor 36 may be arranged to detect light originating from the light source 32 that has been reflected in the body fluid, for example in the vicinity of the point or region outside the housing. The detected light may have been focused from the point or region outside the housing 10 towards the first optical sensor 35 and second optical sensor 36 by one or more lenses 46. Exemplary optical paths are illustrated in FIG. 4 by arrows.

The second linear polarizer 42 is arranged such that a first part of the linearly polarized light emitted from the light source 32 to the region outside the housing 10 is incident on the second linear polarizer 35. In other words, the second linear polarizer 42 is located in an optical path between the light source 32 and the first optical sensor 35, between the region outside the housing 10 and the first optical sensor 35.

The third linear polarizer 43 is arranged such that a second part of the linearly polarized light emitted from the light source 32 to the region outside the housing 10 is incident on the third linear polarizer 43. In other words, the third linear polarizer 43 is located in an optical path between the light source 32 and the second optical sensor 36, between the region outside the housing 10 and the second optical sensor 36.

The first optical sensor 35 is arranged to detect the first part of the linearly polarized light passing from the region outside the housing 10 through the second linear polarizer 42. This first part of the linearly polarized light originated from the light source 32, was linearly polarized in a first plane by the first linear polarizer 41 before being optically rotated by the glucose in the body fluid, passing through the second linear polarizer 42, and being detected by the first optical sensor 35.

The second optical sensor 36 is arranged to detect the second part of the linearly polarized light passing from the region outside the housing 10 through the third linear polarizer 43. This second part of the linearly polarized light originated from the light source 32, was linearly polarized in a first plane by the first linear polarizer 41 before being optically rotated by the glucose in the body fluid, passing through the third linear polarizer 43, and being detected by the second optical sensor 36.

The first optical sensor 35 and second optical sensor 36 are configured to each output an electrical signal based on a detected light intensity, and therefore based on the angle through which the linear plane of polarization of light emitted by the light source 32 has been optically rotated. The complex signal $S_{PD1}$ and complex signal $S_{PD2}$ output by the first optical sensor 35 and second optical sensor 36 respectively can be used to determine the angle α through which the linearly polarized is rotated by the glucose using the following equation:

$$\tan\alpha = \frac{S_{PD2}}{S_{PD1}}$$

By determining a value of α, a value corresponding to the glucose concentration of the body fluid can be determined, as discussed previously.

Signals $S_{PD1}$ and $S_{PD2}$ will be dependent upon factors such as current passing through the light source 32, channel gain, type specific LED radiant intensity, ambient light, the transmission factor of the blood or other body fluid (a function of various factors such as type of food eaten and time since food eaten), and transmittance of the linear polarizer. By providing the additional third linear polarizer 43 and second optical sensor 36, the electrical signals output by the first optical sensor 35 and second optical sensor 36 can be processed to reduce or remove the effects of the aforementioned factors upon which the signals $S_{PD1}$ and $S_{PD2}$ are otherwise dependent, for example to reduce the effects of interference, for example caused by ambient light, noise in electrical components of the implantable device 1, or similar parasitic effects. As such, a more accurate measurement of glucose concentration can be made, that is not dependent upon these factors.

FIG. 5 shows a further embodiment similar to FIG. 4, however here the glucose measurement unit 30 further comprises a second light source 35, which again may comprise one or more LEDs. In a similar manner as discussed with reference to FIG. 4, the light source 32 of FIG. 5 (hereafter referred to as the first light source 32 with respect to FIG. 5) is configured to emit light through the light transmissive part 12 to a (first) region outside the housing 10 while the second light source 35 is configured to emit light through the light transmissive part 12 to a (second) region outside the housing 10. The first region and second region may be identical.

The first linear polarizer 41 of FIG. 5 is arranged to linearly polarize light emitted from the first light source 32 through the light transmissive part 12 in a first polarization plane, this light being emitted to the first region outside the housing 10. The second linear polarizer 42 is arranged to linearly polarize light from the first region outside the housing 10 in a second plane substantially orthogonal to the first plane (i.e. rotated 90° about the optical axis).

The fourth linear polarizer 44 of FIG. 5 is arranged to linearly polarize light emitted from the second light source 35 through the light transmissive part 12 in a third polarization plane, this light being emitted to the second region outside the housing 10.

The third linear polarizer 43 is arranged to linearly polarize light from the second region outside the housing 10 in a fourth plane, wherein the fourth plane is parallel to the third plane (i.e. rotated 0° about the optical axis). The fourth plane may be parallel to the first plane.

The second linear polarizer 42 is arranged such that at least a part of the linearly polarized light emitted from the first light source 32 to the first region outside the housing 10 is incident on the second linear polarizer 42. In other words, the second linear polarizer 42 is located in an optical path between the first light source 32 and the first optical sensor 35, between the first region outside the housing 10 and the first optical sensor 35.

The third linear polarizer 43 is arranged such that at least part of the linearly polarized light emitted from the second light source 35 to the region outside the housing 10 is incident on the third linear polarizer 43. In other words, the fourth linear polarizer 44 is located in an optical path between the second light source 35 and the second optical sensor 36, between the second region outside the housing 10 and the second optical sensor 36.

The first optical sensor 35 is configured to be able to detect the at least part of the linearly polarized light emitted from the first light source 32 (via the first region outside the housing 10), via the second linear polarizer 42. The second optical sensor 36 is configured to be able to detect the at least part of the linearly polarized light emitted from the second light source 35 (via the second region outside the housing 10), via the third linear polarizer 433.

Preferably the first optical sensor 35 is arranged within the implantable device 1 such that it does not detect light emitted by the second light source 35, while the second optical sensor 36 is arranged within the implantable device 1 such that it does not detect light emitted by the first light source 32. This reduces the effects of interference on the electrical signals output by the first optical sensor 35 and second optical sensor 36.

The first optical sensor 35 and second optical sensor 36 are each configured to output an electrical signal based on a detected light intensity, and therefore based on the angle of optical rotation of polarized light from the first light source 32 or second light source 35, as appropriate. The complex signal $S_{PD1}$ and complex signal $S_{PD2}$ output by the first optical sensor 35 and second optical sensor 36 respectively can be used to determine the angle $\alpha$ through which the linearly polarized is rotated by the glucose using the following equation:

$$\tan\alpha = \frac{S_{PD2}}{S_{PD1}}$$

The determined value of $\alpha$ can be used to determine a value corresponding to the glucose concentration of the body fluid, as discussed previously.

By providing the additional third linear polarizer 43, fourth linear polarizer 44, and second optical sensor 36 in comparison to the implantable device 1 of FIG. 3, the electrical signals output by the first optical sensor 35 and second optical sensor 36 can be processed to reduce the effects of interference, for example caused by ambient light. As such, a more accurate measurement of glucose concentration can be made.

Figure 6:
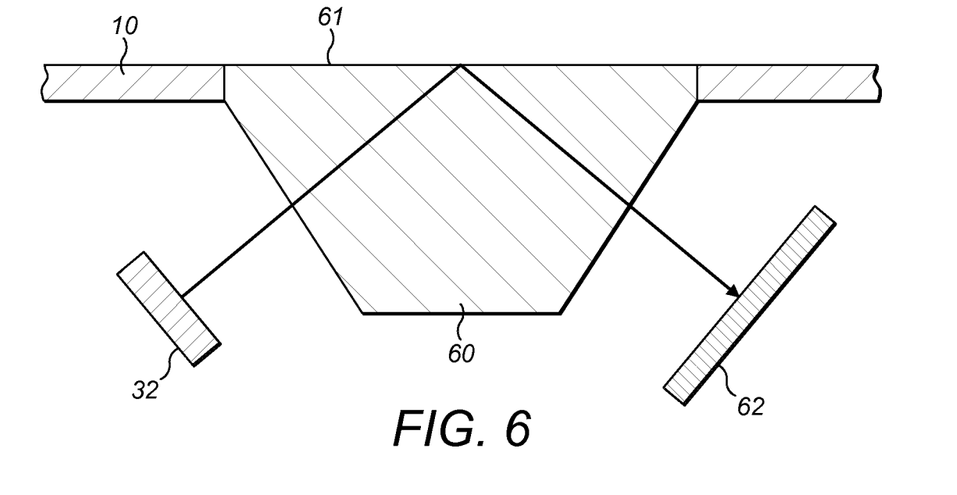
FIG. 6 is a schematic cross-section of part of an implantable device comprising a reflectometer according to embodiments of the present disclosure.

In some embodiments, the glucose measurement unit is a refractometer, wherein the electrical signal output by the optical sensor 34 is based on the refractive index $n_2$ of the body fluid in contact with the light transmissive part 12.

The refractive index $n_2$ of a body fluid containing glucose is a function of (i.e. depends on the) glucose concentration within the body fluid. As glucose concentration of a body fluid varies, so too does the refractive index of the body fluid. The refractive index of a body fluid can be determined using a refractometer. By determining the refractive index of the body fluid, a value of glucose concentration may be determined. This may involve use of a look-up table, as discussed with reference to optical activity.

FIG. 6 shows a partial schematic cross-section of an implantable device 1 in which the glucose measurement unit 30 is a refractometer. The refractometer comprises a prism 60, wherein the light source 32 and the prism 60 are arranged such that the light emitted from the light source 32 is incident on a surface 61 of the prism 60, via the prism 60. In other words, and as shown by the arrows in FIG. 6, the prism 60 and light source 32 are positioned such that light emitted from light source 32 enters prism 60 and travels through the prism 60 until it reaches surface 61 of the prism 60.

Body fluid will be in contact with surface 61 when the implantable device 1 is implanted. As such, the light transmissive part 12 comprises the prism 60.

Depending upon the angle of incidence $\theta_1$ of the light upon the surface 61, a portion of the light emitted from the light source 32 may be reflected at the surface 61 of the prism 60, at the body fluid-prism interface (i.e totally internally reflected). The optical sensor 34 is arranged to detect this reflected portion of the light once it has returned through and exited the prism 60. In particular, the optical sensor 34 is arranged to measure the angle of refraction $\theta_2$ of the (totally internally) reflected light.

FIG. 6 shows the optical sensor 34 as a CCD sensor 62. The location of the reflected light on the CCD sensor 62 can be used to determine the angle of refraction $\theta_2$ and therefore determine the refractive index of the body fluid in contact with the surface 61. The CCD sensor 62 therefore outputs an electrical signal based on the refractive index of the body fluid.

The relationship between the angle of incidence $\theta_1$, angle of refraction $\theta_2$, refractive index $n_1$ of the prism 60 and refractive index $n_2$ of the body fluid is given as:

$$\frac{\sin\theta_1}{\sin\theta_2} = \frac{n_2}{n_1}$$

Thus if the angle of incidence $\theta_1$ and refractive index $n_1$ of the prism 60 are already known, then by measuring the angle of refraction $\theta_2$, a value for the refractive index $n_2$ of the body fluid can be determined. The value for the refractive index of the body fluid can be used to determine a value for the concentration of glucose in the body fluid, for example by comparing the value for the refractive index of the body fluid to a look-up table, or performing additional calculations on the value for the refractive index of the body fluid.

By using a refractometer to measure an angle of refraction, an accurate value of glucose concentration can be determined, since factors such as the absolute brightness of light source 32 and the light transmission of the body fluid will not affect the angle of refraction and hence the determined value of glucose concentration.

In some embodiments, the glucose measurement unit is an infra-red spectrometer. The infrared absorption spectrum of a body fluid containing glucose will vary with glucose concentration. By measuring the infra-red absorption of the body fluid, a value of glucose concentration may be determined. This may involve use of a look-up table, as discussed with reference to optical activity.

Figure 7:
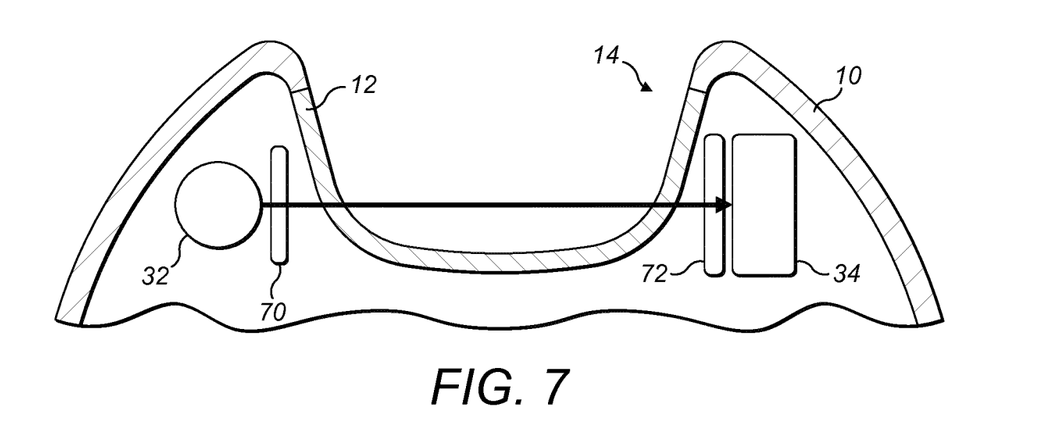
FIG. 7 is a schematic cross-section of part of an implantable device comprising an infra-red spectrometer according to embodiments of the present disclosure.

FIG. 7 shows an embodiment in which the glucose measurement unit is an infra-red spectrometer.

The light emitted by the light source 32 is infra-red light and is emitted through the light transmission part 12 to a region outside the housing 10. The optical sensor 34 is configured to detect infra-red light returned through the light transmissive part 12 from the light source 32, via the region outside the housing 10, and output an electrical signal based on the detected light infra-red light, and thus based on the glucose concentration in the body fluid.

Optionally, the glucose measurement unit 30 comprises a first filter 70 configured to filter the light emitted by the light source 32 such that only light of a particular wavelength passes through the first filter 70 and is emitted through the light transmissive part 12 to the region outside the housing 10. Optionally, the glucose measurement unit 30 comprises a second filter 72 configured to filter the light returned through the light transmissive part 12 from the light source 32, such that only light of a particular wavelength passes through the second filter 72 and is detected by the optical sensor 34. The optical sensor 34 may be configured to detect a variable band of wavelengths of light. The band of wavelengths detected by the optical sensor 34 may be adjusted by changing a voltage applied to the optical sensor 34.

The present disclosure also relates to a system comprising an external wireless communication device 2 and an implantable device 1 according to any of the aforementioned embodiments. FIG. 8 shows such a system when the implantable device 1 has been implanted into a blood vessel 3 of a patient 4 (such as a human or animal).

In a similar manner to the wireless communication module 20 of the implantable device 1, the external wireless communication device 2 comprises an antenna, power supply and control unit (not shown). During use, the external wireless communication device 2 may be brought into close proximity of the implantable device 1. If the implantable device 1 has been implanted into a patient 4, this may involve bringing the external wireless communication device 2 into the vicinity of the skin 5 of the patient 4, for example within a distance d of less than around 2 cm from the skin 5.

The external wireless communication device 2 wirelessly transmits power to the implantable device 1 by electromagnetic induction between the antenna of the external wireless communication device 2 and the antenna 22 of the implantable device 1. A current is induced in the antenna 22 of the implantable device 1, providing power to any electrical circuitry within the device, such as the glucose measurement unit 30.

Responsive to receiving the power, or responsive to receiving an additional wireless signal transmitted by the external communication device 2 to the implantable device 1, the implantable device 1 proceeds with measuring the glucose concentration of body fluid in contact with the housing 10 of the implantable device 1. The light source 32 of the implantable device 1 emits light towards the light transmissive part 12 of the housing 10 of the implantable device 1. The optical sensor 34 of the implantable device 1 detects light returned through the transmissive part 12, and outputs an electrical signal based on the detected light. The wireless communication module 20 of the implantable device 1 is configured to wirelessly transmit a signal based on the electrical signal to the external wireless communication device 2. The signal wirelessly transmitted to the external wireless communication device 2 by the implantable device 1 may be processed (for example by the external wireless communication device 2) to determine a value of glucose concentration for the body fluid.

The present disclosure also relates to a method of performing any of the aforementioned steps in relation to the implantable device 1 and external wireless communication device 2.

Figure 9:
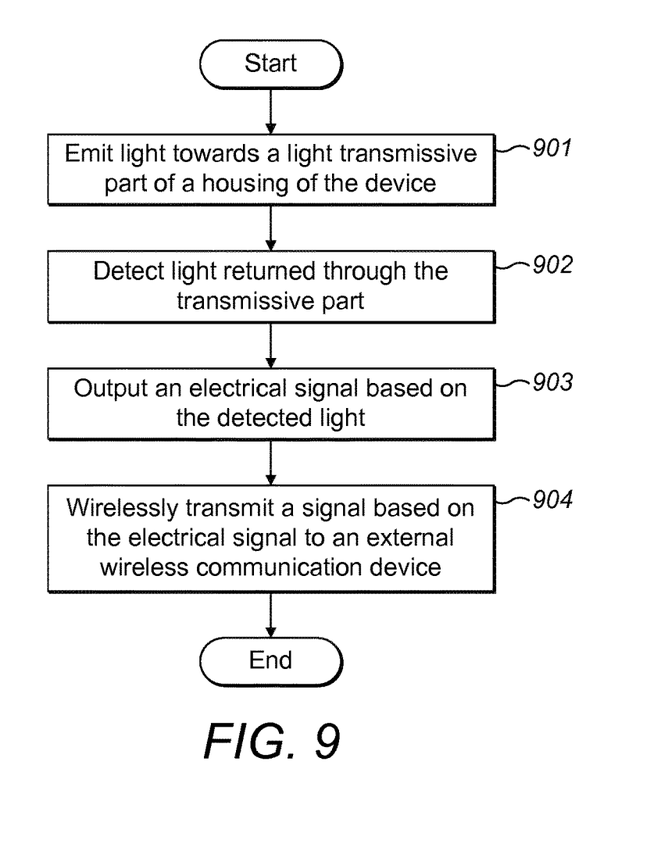
FIG. 9 is a flowchart illustrating a method for determining glucose concentration in a body fluid according to aspects of the present disclosure.

FIG. 9 shows a method according to embodiments of the present disclosure. At step 901, light is emitted by a light source 32 of an aforementioned implantable device 1 towards a light transmissive part 12 of a housing 10 of the implantable device 1. At step 902, an optical sensor 34 of the implantable device 1 detects light returned through the light transmissive part 12 from the light source 32. At step 903, an electrical signal based on the detected light is output by the optical sensor 34. At step 904, a wireless communication module 20 of the implantable device 1 wirelessly transmits a signal based on the electrical signal to an external wireless communication device 1. As discussed previously, the signal wirelessly transmitted to the external wireless communication device 2 by the implantable device 1 may be processed (for example by the external wireless communication device 2) to determine a value of glucose concentration for the body fluid.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codeable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts. Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

Although claims have been formulated in this application to particular combinations of features, it should be understood that the scope of the disclosure also includes any novel features or any novel combinations of features disclosed herein either explicitly or implicitly or any generalization thereof, whether or not it relates to the same disclosure as presently claimed in any claim and whether or not it mitigates any or all of the same technical problems as does the present disclosure. The applicant hereby gives notice that new claims may be formulated to such features and/or combinations of features during the prosecution of the present application or of any further application derived therefrom.

Although several embodiments have been shown and described, it would be appreciated by those skilled in the art that changes may be made in these embodiments without departing from the principles of the disclosure, the scope of which is defined in the claims.

The invention claimed is:

1. An implantable device for measuring a glucose concentration of a body fluid, the implantable device comprising:
    a housing containing a glucose measurement unit, the glucose measurement unit comprising:
        a first light source configured to emit light from inside the housing towards a light transmissive part of the housing,
        a first linear polarizer configured to linearly polarize the light emitted from the first light source to provide a first polarized light emitted through the light transmissive part to a first region outside the housing,
        a second linear polarizer configured to provide a second polarized light by linearly polarizing a first returned light that is returned to the housing through the light transmissive part of the housing, wherein the first returned light includes a first part of the first polarized light that returned from the first region outside the housing and has been optically rotated,
        a first optical sensor configured to detect the second polarized light, and output a first electrical signal based on the detected second polarized light,
        a third linear polarizer configured to provide a third polarized light by linearly polarizing a second returned light that is returned to the housing through the light transmissive part, wherein the second returned light includes a second part of the first polarized light that has returned to the light transmissive part of the housing, and
        a second optical sensor configured to detect the third polarized light, and output a second electrical signal based on the detected third polarized light; and
    a wireless communication module configured to wirelessly transmit a wireless signal to an external wireless communication device, the wireless signal being based on the first electrical signal and the second electrical signal.

2. The implantable device according to claim 1, wherein the wireless communication module is configured to wirelessly receive power from the external wireless communication device.

3. The implantable device according to claim 1, wherein the implantable device is dimensioned to be implantable into a human blood vessel.

4. The implantable device according to claim 1, wherein an outer surface of the housing comprises a recess, and wherein the recess comprises at least part of the light transmissive part.

5. The implantable device according to claim 1, further comprising at least one lens arranged to focus the light emitted from the first light source towards a point outside the housing.

6. The implantable device according to claim 1,
wherein the first linear polarizer is arranged to linearly polarize the light emitted from the first light source in a first plane,
wherein the second linear polarizer is arranged to linearly polarize the first returned light in a second plane substantially orthogonal to the first plane,
wherein the third linear polarizer is arranged to linearly polarize the second returned light in a third plane, wherein the third plane is parallel to the first plane,
wherein the second linear polarizer is arranged such that the first part of the first polarized light is incident on the second linear polarizer, and
wherein the third linear polarizer is arranged such that the second part of the first polarized light is incident on the third linear polarizer.

7. The implantable device according to claim 1, wherein the glucose measurement unit further comprises:
a second light source configured to emit light through the light transmissive part to a second region outside the housing,
wherein the first linear polarizer is arranged to linearly polarize the light emitted from the first light source in a first plane,
wherein the second linear polarizer is arranged to linearly polarize the first returned light in a second plane substantially orthogonal to the first plane; and
a fourth linear polarizer that is arranged to linearly polarize the light emitted from the second light source in a third plane
wherein third linear polarizer that is arranged to linearly polarize light returned from the second region to the housing in a fourth plane, wherein the fourth plane is parallel to the third plane, and
wherein the second linear polarizer is arranged such that at least part of the first returned light is incident on the second linear polarizer,
wherein the third linear polarizer is arranged such that at least part of the linearly polarized light emitted from the second light source to the second region outside the housing is incident on the fourth linear polarizer, and
wherein the second optical sensor is configured to detect the at least part of the linearly polarized light emitted from the second light source, via the third linear polarizer.

8. The implantable device according to claim 1, wherein the glucose measurement unit comprises a refractometer.

9. The implantable device according to claim 8,
wherein the refractometer comprises a prism,
wherein the first light source and the prism are arranged such that the light emitted from the first light source is incident on a surface of the prism, and
wherein the first optical sensor is arranged to detect a portion of the light emitted from the first light source that is reflected at the surface of the prism.

10. The implantable device according to claim 1,
wherein, the glucose measurement unit further comprises an infra-red spectrometer,
wherein the light emitted by the first light source comprises infra-red light and is emitted through a light transmission part to the first region outside the housing, and
wherein the first optical sensor is configured to detect infra-red light returned through the light transmissive part from the first light source, via the first region outside the housing and to output the first electrical signal based on the infra-red light that has been detected.

11. The implantable device according to claim 1, further comprising a temperature sensor, wherein the wireless communication module is configured to wirelessly transmit a temperature signal based on a temperature measured by the temperature sensor to the external wireless communication device.

12. The implementable device of claim 1, wherein the second linear polarizer is arranged to linearly polarize the first returned light in a first plane, and the third linear polarizer is arranged to linearly polarize the second returned light in a second plane, and
wherein first plane is non-parallel with the second plane.

13. A system comprising:
an implantable device for measuring a glucose concentration of a body fluid, the implantable device comprising:
a housing containing a glucose measurement unit, the glucose measurement unit comprising:
a first light source configured to emit light from inside the housing towards a light transmissive part of the housing,
a first linear polarizer configured to linearly polarize the light emitted from the first light source to provide a first polarized light emitted through the light transmissive part to a first region outside the housing,
a second linear polarizer configured to provide a second polarized light by linearly polarizing a first returned light that is returned to the housing through the light transmissive part of the housing, wherein the first returned light includes a first part of the first polarized light that returned from the first region outside the housing and has been optically rotated,
a first optical sensor configured to detect the second polarized light, and output a first electrical signal based on the detected second polarized light,
a third linear polarizer configured to provide a third polarized light by linearly polarizing a second returned light that is returned to the housing through the light transmissive part, wherein the second returned light includes a second part of the first polarized light that has returned to the light transmissive part of the housing,
a second optical sensor configured to detect the third polarized light, and output a second electrical signal based on the detected third polarized light, and a wireless communication module; and an external wireless communication device, wherein the wireless communication module of the implantable device is configured to wirelessly transmit a wireless signal to the external wireless communication device, the wireless signal being based on the first electrical signal and the second electrical signal.

14. The system of claim 13, wherein the second linear polarizer is arranged to linearly polarize the first returned light in a first plane, and the third linear polarizer is arranged to linearly polarize the second returned light in a second plane, and wherein first plane is non-parallel with the second plane.

15. The system according to claim 13, wherein the external wireless communication device comprises a smartphone.

16. The system according to claim 13, wherein the wireless communication module is configured to wirelessly receive power from the external wireless communication device.

17. The system according to claim 13, wherein an outer surface of the housing comprises a recess, and wherein the recess comprises at least part of the light transmissive part.

18. The system according to claim 13, wherein the implantable device further comprises at least one lens arranged to focus the light emitted from the first light source towards a point outside the housing.

19. The system according to claim 13, wherein the glucose measurement unit further comprises a refractometer.

20. A method comprising:

providing an implantable device for measuring a glucose concentration of a body fluid, the implantable device comprising:

a housing containing a glucose measurement unit, the glucose measurement unit comprising:

a first light source configured to emit light from inside the housing towards a light transmissive part of the housing, a first optical sensor configured to detect light returned through the light transmissive part of the housing from the first light source and to output a first electrical signal based on the light that has been detected by the first optical sensor, a second optical sensor configured to detect light returned through the light transmissive part and to output a second electrical signal based on the light that has been detected by the second optical sensor, and a wireless communication module configured to wirelessly communicate with an external wireless communication device, emitting light, by the first light source of the implantable device towards the light transmissive part of the housing of the implantable device, wherein the light emitted from the first light source is linearly polarized by a first linear polarizer and emitted through the light transmissive part to a first region outside the housing;

detecting, by the first optical sensor of the implantable device, light returned through the light transmissive part from the first light source, wherein the first optical sensor is configured to detect linearly polarized light returned through the light transmissive part from the first region outside the housing once the linearly polarized light has been optically rotated, wherein the linearly polarized light detected by the first optical sensor has been linearly polarized by a second linear polarizer;

detecting, by the second optical sensor of the implantable device, linearly polarized light returned through the light transmissive part, wherein the linearly polarized light detected by the second optical sensor has been linearly polarized by a third linear polarizer;

outputting, by the first optical sensor, a first electrical signal based on the light that has been detected by the first optical sensor;

outputting, by the second optical sensor, a second electrical signal based on the light that has been detected by the second optical sensor; and wirelessly transmitting, by the wireless communication module of the implantable device, a wireless signal based on the first electrical signal and the second electrical signal to an external wireless communication device.

* * * * *

UNITED STATES PATENT AND TRADEMARK OFFICE
CERTIFICATE OF CORRECTION

PATENT NO. : 11,730,404 B2
APPLICATION NO. : 16/765231
DATED : August 22, 2023
INVENTOR(S) : Thomas Klemm Page 1 of 1

It is certified that error appears in the above-identified patent and that said Letters Patent is hereby corrected as shown below:

In the Claims

Column 21, Line 48, Claim 7, after "wherein", insert -- the --

Column 22, Line 26, Claim 12, delete "implementable" and insert -- implantable --

Signed and Sealed this
Twenty-second Day of July, 2025

Coke Morgan Stewart
*Acting Director of the United States Patent and Trademark Office*